United States Patent

Taylor et al.

[11] Patent Number: 5,952,652
[45] Date of Patent: Sep. 14, 1999

[54] ION MOBILITY SPECTROMETERS

[75] Inventors: Stephen J. Taylor, Amersham; Robert B. Turner, Chesham, both of United Kingdom

[73] Assignee: Graseby Dynamics Limited, Herfordshire, United Kingdom

[21] Appl. No.: 08/952,600

[22] PCT Filed: May 23, 1996

[86] PCT No.: PCT/GB96/01248

§ 371 Date: Feb. 20, 1998

§ 102(e) Date: Feb. 20, 1998

[87] PCT Pub. No.: WO96/37773

PCT Pub. Date: Nov. 28, 1996

[30] Foreign Application Priority Data

May 23, 1995 [GB] United Kingdom .................... 9510405

[51] Int. Cl.$^6$ .................................................. H01J 49/40
[52] U.S. Cl. .......................... 250/286; 250/287; 250/289
[58] Field of Search .................................. 250/286, 287, 250/281, 282, 288, 289

[56] References Cited

U.S. PATENT DOCUMENTS

| | | | |
|---|---|---|---|
| 4,551,624 | 11/1985 | Spangler et al. | 250/287 |
| 5,283,199 | 2/1994 | Bacon, Jr. et al. | 250/286 |
| 5,475,217 | 12/1995 | Bradshaw | 250/287 |

*Primary Examiner*—Kiet T. Nguyen
*Attorney, Agent, or Firm*—Price, Heneveld, Cooner, Dewitt and Litton

[57] ABSTRACT

An ion mobility spectrometer includes a spectrometer housing (10) and, within the housing, an ion mobility spectrometer cell (12), a volume of vapour absorbent material (30), and a fan (38) for inducing a flow of recirculating cleaning air through the cell (12) and the absorbent material (30). The vapour absorbent material is held in close proximity with the cell, providing the possibility of constructing a miniature instrument without the need for any external air supply.

17 Claims, 1 Drawing Sheet

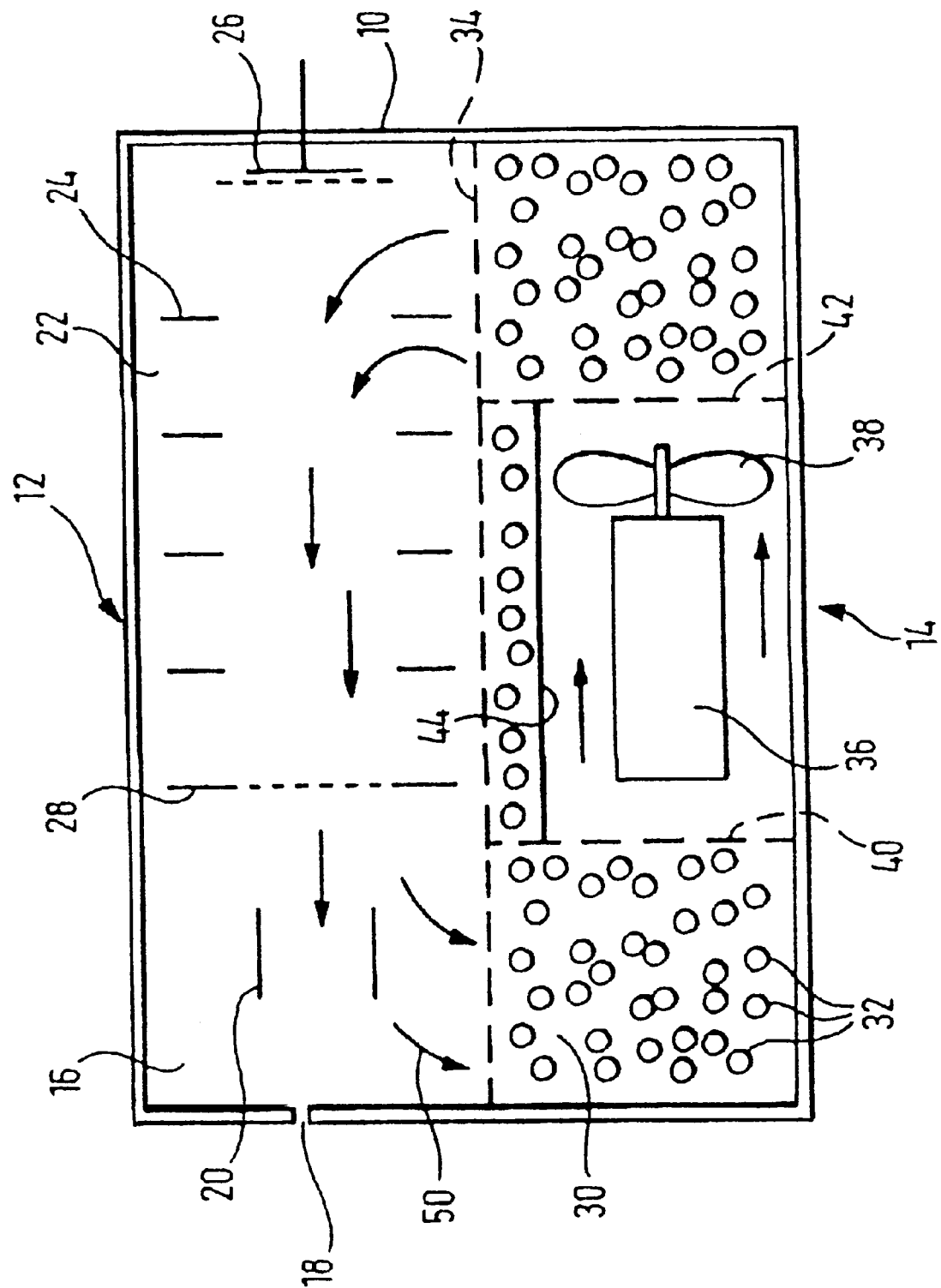

ION MOBILITY SPECTROMETERS

BACKGROUND OF THE INVENTION

The present invention relates to ion mobility spectrometers and more particularly to ion mobility spectrometers incorporating a body of vapour absorbent material such as a molecular sieve pack within the instrument housing.

It is well known that for correct operation at least the drift space of an ion mobility spectrometer cell needs to contain gas that is free of contaminants such as residual sample vapours. For correct operation there is also a need to maintain the level of moisture vapour, which may also be regarded as a contaminant, at well below that of ambient atmosphere. In prior art instruments such conditions are typically achieved by sweeping the drift space either with a flow of clean dry gas, which may come from an air-line, or by use of a complex re-circulating air system such as is described in U.S. Pat. No. 4,317,995.

However in a recent development, the subject of our co-pending application No WO93/06476, the necessary clean dry conditions are maintained within an ion mobility spectrometer by means of a diffusion process, in which a body of molecular sieve material is held in intimate contact with the internal volume of the IMS cell. As the barrier between cell and molecular sieve may only be a thin sheet of mesh, any contaminant vapours within the cell will diffuse towards the sieve pack where they are absorbed and the cell volume thus kept clean and dry.

The system described works well in many applications, particularly if the sample vapour to be analysed is drawn into the cell intermittently allowing time for residual sample vapour and any water vapour drawn in with it to diffuse to the molecular sieve pack and to be absorbed before the next sample is drawn into the cell. By obviating the need either for an external air supply or for a complex recirculatory system, use of a molecular sieve pack arrangement within the ion mobility spectrometer casing permits the design of small and simple ion mobility spectrometer instruments, ideally suited for use in miniature hand-held or body-worn IMS detectors.

However if such instruments are employed for continuous use, problems may arise as a result of the relatively long clear-down time, that is the time taken for the molecular sieve pack to cleanse the internal atmosphere of the cell to a level at which a further sample may be accurately measured.

Additionally, problems may be encountered with the absorbing capacity of the molecular sieve under conditions of continuous use. In the diffusion cleaning process, over a short timescale only those layers of the sieve nearest the IMS cell space are active, as the contaminant vapours do not reach the inner layers of the sieve. Consequently after a period of continuous use the absorbing capacity of the active layers becomes exhausted and the clear-down time of the instrument increases. If the instrument is then switched off, preventing the intake of any further sample, an equilibrium of the absorbed vapours within the molecular sieve pack occurs and the active layers become absorbent again.

Thus whilst a simple IMS instrument incorporating a molecular sieve pack and a vapour diffusion cleansing process is acceptable for intermittent or infrequent use, for example for periodic testing of an ambient atmosphere for trace of a possible contaminant or contaminants, it is less suitable for continuous use.

It is an object of the present invention to overcome the shortcomings of such an ion mobility instrument employing a vapour absorbent material, such as molecular sieve pack, in intimate contact with the drift space of the internal volume of the IMS cell, as the cleansing and/or dessicating means, whilst retaining the advantages offered by such an instrument.

SUMMARY OF THE INVENTION

According to one aspect the invention consists in the provision in such an instrument of means to induce a flow of air, or other ambient atmosphere, within the instrument between the drift space of the IMS cell and the vapour absorbent material, thereby to draw contaminant vapours from the IMS cell into the body of vapour absorbent material.

A system in accordance with the invention provides the compactness and simplicity achieved by the use of vapour absorbent e.g. molecular sieve, cleansing, whilst adding the advantage of fast clear-down, permitting either continuous sampling or more frequent sampling than has hitherto been possible with such instruments.

BRIEF DESCRIPTION OF THE DRAWINGS

The invention is illustrated in and further described with reference to the accompanying drawing which illustrates diagramatically the layout of a self-contained miniature IMS instrument in accordance with the invention.

DESCRIPTION OF THE PREFERRED EMBODIMENTS

Referring to the drawing, an IMS instrument comprises an outer casing 10, sub-divided into a portion containing the IMS cell 12, and a portion containing the molecular sieve pack 14.

The IMS cell 12 comprises an ionisation region 16, with a sample inlet aperture 18, an ionising electrode 20, and a drift region 22, provided with a series of accelerator electrodes 24 and a collector electrode 26. The ionisation and drift regions are separated by a gate electrode 28, controlling the entry into drift region 22 of sample ions generated in the ionisation region 16.

Operation of the IMS cell under the control of external electronic circuitry is well known in the art and, as it forms no part of the present invention, will not be further described.

The molecular sieve pack 14 comprises a sieve structure 30 containing sieve beads 32 retained within the sieve structure 30 by means of a mesh 34 in close contact with the interior of the IMS cell 12.

A suitable molecular sieve material would be a zeolite such as 13X, 10A or 5A, with acceptable bead sizes ranging from 1 mm to 4 mm in diameter. The typical absorption capacity of such a sieve material is 10% to 20% by weight of water.

The body of the sieve structure 30 is constructed to permit a small electric motor 36 driving a fan 38 to be mounted within it. Motor 36 and fan 38 are separated from the sieve structure 30 by mesh walls 40 and 42, or other filter devices, and an impermeable inner wall 44.

Fan 38 may be either of an axial or centrifugal type, functioning to induce a flow of air in a re-circulating manner between the body of the sieve structure 30 and the volume of the IMS cell 12, drawing water vapour and other contaminants from one end of the IMS cell 12 into the body of the sieve structure 30 for absorption by sieve beads 32, and returning clean dry air to the other end of IMS cell 12. The air flow is represented in the drawing by the arrows 50.

In operation a sample of ambient atmosphere in the region of the pin-hole inlet 18 is drawn, together with any detectable vapours it contains, into the ionisation region 16 of IMS cell 12, against the internal air flow 50, as the result of a momentary pressure drop within the casing 10, induced for example by a moving diaphragm, such as that of a miniature loudspeaker, mounted upon and in communication with interior space of casing 10. Such an arrangement is illustrated and described in our co-pending application No WO93/01485.

The vapours are ionised, the ionisation products injected into the drift region 22 under control of gate electrode 28, and the ionisation products of interest drawn towards collector electrode 26 under the influence of the electric field established by the accelerator electrodes 24. Unwanted ionisation products, together with surplus sample vapour and water vapour are swept into the sieve structure 30 entrained in the air flow 50 generated by fan 38.

A fan motor 36 sufficient to induce an airflow of several hundred milliliters per minute through the combined sieve structure 30 and meshes 34, 40, and 42, has a size approximately 15 mm by 7 mm by 7 mm, with a fan 38 of about 12 mm in diameter and 2 mm axial length. The power requirement for such an electric motor and fan is about 30 mW, representing an insignificant demand upon the battery required to power the other operating functions of the IMS instrument.

In an instrument of the type described, with a pin-hole aperture inlet and with a motor-driven fan of the type described, the clear-down time for the cell from sample intake, is typically less than 0.25 seconds for low sample vapour concentrations, and less than about 2 seconds for high sample vapour concentrations. These figures are considerably less than for a standard IMS system with a complex internal re-circulating air flow system, employing a membrane inlet system, and less than for a pin-hole aperture inlet instrument such as described, but without the fan-induced airflow arrangement.

If the pin-hole inlet aperture 18 is provided with an injection system such as is described in our copending PCT Application No WO93/01485, the operation of fan 38 and the electrically driven inlet injection system may advantageously be synchronised under control of the instrument's electronic control system, for most effective operation.

With synchronisation, fan motor 36 may be switched off when the injection system has been powered to inject a sample into the ionisation region 16, allowing the sample to be processed through cell 12, before being switched on again to initiate airflow to clear the cell 12 of surplus sample vapour and other contaminants prior to the next sample injection.

Although particular reference has been made to the use of molecular sieve materials in the form of sieve packs as the vapour absorbent material to perform the cleansing and drying operations within the casing of the instrument, such materials being of particular efficacy for the purpose, other materials may also be used for the purpose, such as, for example, activated charcoal, determined by the application, and the nature of the vapours to be extracted.

A miniature IMS instrument in accordance with the invention and generally as described with relation to the accompanying drawing, has been constructed with overall external dimensions of 65 mm long by 55 mm wide and 30 mm deep, with an internal molecular sieve pack 65 mm long by 25 mm wide and 30 mm in depth.

It will be appreciated that various modifications may be made to the instrument described herein without exceeding the scope of the invention, for example means other than a fan may be used to cause the internal circulation of air or other ambient atmosphere from cell space to vapour absorbent material, and means other than the injection system referred to may be used to draw ambient atmosphere from the surroundings into the casing of the instrument.

We claim:

1. An ion mobility spectrometer including a spectrometer housing subdivided into a first portion including an ion mobility spectrometer cell and a second portion including a volume of vapour absorbent material, the vapour absorbent material extending the length of the cell and being adjacent thereto, thereby allowing contaminant vapours within the cell to diffuse into the vapour absorbent material; the spectrometer further including a gas recirculator within the second portion of the housing for inducing a recirculating flow of gas within the housing through the cell and the vapour absorbent material.

2. An ion mobility spectrometer as claimed in claim 1 in which the absorbent material is positioned adjacent the cell and separated therefrom by a mesh through which the gas may flow.

3. An ion mobility spectrometer as claimed in claim 1 in which the absorbent material includes a molecular sieve material.

4. An ion mobility spectrometer as claimed in claim 3 in which the molecular sieve material comprises a zeolite.

5. An ion mobility spectrometer as claimed in claim 3 in which the absorbent material comprises a plurality of absorbent beads.

6. An ion mobility spectrometer as claimed in claim 3 in which the cleansing gas is air.

7. An ion mobility spectrometer as claimed in claim 6 in which the gas recirculator for inducing a flow of cleansing air is contained with the volume of vapour absorbent material.

8. An ion mobility spectrometer as claimed in claim 1 in which the absorbent material comprises a plurality of absorbent beads.

9. An ion mobility spectrometer as claimed in claim 8 in which the beads are between about 1 and 4 mm in diameter.

10. An ion mobility spectrometer as claimed in claim 1 in which the cleansing gas is air.

11. An ion mobility spectrometer as claimed in claim 10 in which the gas recirculator for inducing a flow of cleansing gas comprises a fan.

12. An ion mobility spectrometer as claimed in claim 1 in which the gas recirculator for inducing a flow of cleansing gas is contained within the volume of vapour absorbent material.

13. An ion mobility spectrometer as claimed in claim 1 in which the means for inducing a flow of cleansing gas comprises a fan.

14. An ion mobility spectrometer as claimed in claim 1 in which the absorbent material is positioned adjacent the cell and separated therefrom by a mesh through which the gas may flow.

15. An ion mobility spectrometer as claimed in claim 1 in which the absorbent material includes a molecular sieve material.

16. An ion mobility spectrometer as claimed in claim 15 in which the molecular sieve material comprises a zeolite.

17. An ion mobility spectrometer including a spectrometer housing and within the housing, an ion mobility spectrometer cell, a volume of vapour absorbent material extending the length of the cell including a plurality of absorbent beads comprising a zeolite molecular sieve material, and a fan inducing a flow of cleansing gas through the cell and the vapour absorbent material.

* * * * *